United States Patent
Collins et al.

(10) Patent No.: US 12,343,205 B2
(45) Date of Patent: Jul. 1, 2025

(54) SYSTEM AND METHOD FOR MEDICAL NAVIGATION

(71) Applicants: INSTITUT HOSPITALO-UNIVERSITAIRE DE STRASBOURG, Strasbourg (FR); INSTITUT DE RECHERCHE CONTRE LES CANCERS DE L'APPAREIL DIGESTIF, Strasbourg (FR)

(72) Inventors: Toby Collins, Strasbourg (FR); Leonardo Sosa Valencia, Strasbourg (FR); Alexandre Hostettler, Strasbourg (FR); Caroline Trompf, Strasbourg (FR); Jacques Marescaux, Scharrachbergheim-Irmstett (FR)

(73) Assignees: INSTITUT HOSPITALO-UNIVERSITAIRE DE STRASBOURG, Strasbourg (FR); INSTITUT DE RECHERCHE CONTRE LES CANCERS DE L'APPAREIL DIGESTIF, Strasbourg (FR)

( * ) Notice: Subject to any disclaimer, the term of this patent is extended or adjusted under 35 U.S.C. 154(b) by 261 days.

(21) Appl. No.: 17/421,570

(22) PCT Filed: Jan. 17, 2020

(86) PCT No.: PCT/EP2020/051193
§ 371 (c)(1),
(2) Date: Jul. 8, 2021

(87) PCT Pub. No.: WO2020/148450
PCT Pub. Date: Jul. 23, 2020

(65) Prior Publication Data
US 2022/0079557 A1 Mar. 17, 2022

Related U.S. Application Data

(60) Provisional application No. 62/793,963, filed on Jan. 18, 2019.

(51) Int. Cl.
*G06T 7/30* (2017.01)
*A61B 8/00* (2006.01)
(Continued)

(52) U.S. Cl.
CPC .............. *A61B 8/4254* (2013.01); *A61B 8/12* (2013.01); *A61B 8/463* (2013.01); *G06T 7/0012* (2013.01);
(Continued)

(58) Field of Classification Search
CPC ............ A61B 1/0005; A61B 2034/105; A61B 2034/2051; A61B 2034/2061;
(Continued)

(56) References Cited

U.S. PATENT DOCUMENTS

| | | | | |
|---|---|---|---|---|
| 5,515,853 A * | 5/1996 | Smith | ...................... | A61B 5/287 128/916 |
| 2009/0287089 A1* | 11/2009 | Spector | .................. | A61B 8/483 600/466 |

(Continued)

FOREIGN PATENT DOCUMENTS

EP 3 170 456 A1 5/2017

OTHER PUBLICATIONS

Lucian Gheorghe Gruionu et al., "A novel fusion imaging system for endoscopic ultrasound," Jan.-Feb. 2016, Endoscopic Ultrasound, vol. 5, pp. 35-42 (Year: 2016).*

(Continued)

*Primary Examiner* — Ashley K Buran
*Assistant Examiner* — Maria Christina Talty
(74) *Attorney, Agent, or Firm* — Pillsbury Winthrop Shaw Pittman LLP

(57) ABSTRACT

A system for medical navigation includes an echo-endoscope configured to acquire a real-time ultrasound signal and/or a video signal; a tracking system or device configured to track a distal tip of the echo-endoscope in space; a user interface and a display; computing and storing system containing pre-operative radiologic data of a patient; wherein the computing and storing system is configured to perform a registration between real-time intra-operative data and the pre-operative radiologic data and the display is configured to provide to the user a navigation view integrating real-time intra-operative data view within the pre-operative radiologic data based on said registration.

9 Claims, 3 Drawing Sheets

(51) Int. Cl.
| | |
|---|---|
| *A61B 8/12* | (2006.01) |
| *G06T 7/00* | (2017.01) |
| *G06T 7/20* | (2017.01) |
| *G16H 20/40* | (2018.01) |
| *G16H 30/40* | (2018.01) |
| *G16H 40/63* | (2018.01) |
| *A61B 90/00* | (2016.01) |

(52) U.S. Cl.
CPC ................ *G06T 7/20* (2013.01); *G06T 7/30* (2017.01); *G16H 20/40* (2018.01); *G16H 30/40* (2018.01); *G16H 40/63* (2018.01); *A61B 8/4416* (2013.01); *A61B 8/467* (2013.01); *A61B 2090/363* (2016.02); *A61B 2090/364* (2016.02); *G06T 2207/10068* (2013.01); *G06T 2207/10132* (2013.01)

(58) Field of Classification Search
CPC ........ A61B 2090/363; A61B 2090/364; A61B 2090/365; A61B 2090/378; A61B 34/20; A61B 34/25; A61B 8/0883; A61B 8/12; A61B 8/4245; A61B 8/4254; A61B 8/4416; A61B 8/463; A61B 8/467; A61B 8/5261; G06T 2207/10068; G06T 2207/10132; G06T 7/0012; G06T 7/20; G06T 7/30; G16H 20/40; G16H 30/40; G16H 40/63

See application file for complete search history.

(56) References Cited

U.S. PATENT DOCUMENTS

| | | | |
|---|---|---|---|
| 2014/0142422 A1* | 5/2014 | Manzke | .................. A61B 8/12 600/424 |
| 2015/0086956 A1 | 3/2015 | Savitsky et al. | |
| 2019/0307516 A1 | 10/2019 | Schotzko et al. | |

OTHER PUBLICATIONS

Johns Hopkins Medicine, "Upper GI Endoscopy," 2015 (Year: 2015).*
"Ascension Technology Corporation Introduces: microBIRD," 2004 (Year: 2004).*
International Search Report as issued in International Patent Application No. PCT/EP2020/051193, dated Jun. 29, 2020.
Gruionu, L. G., et al., "A novel fusion imaging system for endoscopic ultrasound," Endoscopic Ultrasound / NCBI—National Center for Biotechnology Information, Feb. 2016, URL:https://www.ncbi.nlm.nih.gov/pmc/articles/PMC4770620/pdf/EUS-5-35.pdf, [retrieved on Jun. 12, 2020], 8 pages.
Vosburgh, K. G., et al., "EUS with CT improves efficiency and structure identification over conventional EUS," Gastrointestinal Endoscopy, vol. 65, No. 6, Apr. 2007, pp. 866-870.

* cited by examiner

SYSTEM AND METHOD FOR MEDICAL NAVIGATION

CROSS-REFERENCE TO RELATED APPLICATIONS

This application is the U.S. National Stage of PCT/EP2020/051193, filed Jan. 17, 2020, which in turn claims priority to U.S. provisional patent application No. 62/793,963 filed Jan. 18, 2019. The content of these applications are incorporated herein by reference in their entirety.

TECHNICAL FIELD OF THE INVENTION

The invention belongs to the field of the medical devices and systems for medical navigation comprising the registration of several types of data. A first object of the invention is a device for medical navigation comprising the registration of radiological data and ultrasound data. A second object of the invention is a method for medical navigation comprising the registration of radiological data and ultrasound data.

STATE OF THE ART

Endoscopic Ultrasound (EUS) is an important and increasingly used medical procedure for imaging and diagnostics in the upper digestive tract. An EUS is basically a gastroscope system with an ultrasound (US) sensor attached at the tip, the endoscopic tower comprising an US unit. Both the video feed and the US feed are displayed to the user. EUS provides low-cost multi-modal imaging at close proximity of both surface and subsurface structures, in high resolution and with minimal invasion. However, EUS is a difficult technique to master by endosonographers and highly operator dependent.

The difficulty stems from two main navigational difficulties. First, the EUS probe generates videos with a small spatial window (typically less than 10 cm in width). This provides excellent spatial resolution, but a global understanding of where the probe is with respect to the patient must still be mentally performed by the endosonographers, which is challenging. The second difficulty involves mechanical control: EUS requires a flexible scope that is mechanically controlled at the proximal end. This makes precise positioning and localization of the EUS tip difficult.

The above challenges combine to make EUS very difficult for non-experts, taking many years (more than 5000 procedures) to achieve high proficiency. Fusion between a pre-procedure Computer Tomography (CT) or Magnetic Resonance Image (MRI) slices set and intra-procedural live US images has been proposed in the past. These systems rely on a US probe being tracked in space and involve a registration step between the CT or MRI slices set and the live US images. In commercial navigation systems with trans-abdominal US probes, such as the Siemens ACUSON S3000™ Ultrasound System, the registration is completed in the following way: the sonographer selects precise anatomical landmarks in the CT or MRI image set and manually completes the registration by displaying the anatomical landmark using the US system on the patient, and then selects within the displayed image the exact locus of the landmark. The system then registers the two images. This registration process is adapted for radiologists mastering both the US system and CT or MRI slices set: it requires the user to understand CT or MRI slices sets and necessitates the user to be capable of displaying an image of an anatomical region requested using an US system.

While this has proven to be efficient for hand-controlled US probes, this approach is impossible to implement in the EUS setting. In fact, navigating a EUS scope to a pre-determined area of the body represents a serious challenge requiring expert skills and guidance systems are most needed for novices.

The document US 2015/0086956A1 describes a device comprising a co-registration and navigation system in which 3D and/or 2D ultrasound images are displayed alongside virtual images of a patient and/or CT or MRI scans, or other similar imaging techniques used in the medical field.

This system is useful for offline training of operators, based on pre-registered US and radiological data. It does not provide any technical solution for real-time registration and in particular it is not useful for real-time navigation of an EUS scope.

The document US 2019/0307516 describes a system for guiding an instrument through a region of a patient and a method of using the system.

Nevertheless, this system is not adapted to overcome the difficulties of guiding a EUS scope to a given location and does not solve the technical problems mentioned above.

It is an object of the present disclosure to overcome these limitations by introducing a novel guidance system for EUS navigation based on image fusion and usable by novices.

GENERAL SUMMARY OF THE INVENTION

An object of the invention is a system for medical navigation comprising:
- an echo-endoscope configured to acquire a real-time ultrasound signal and/or a video signal;
- a tracking system or device configured to track a distal tip of the echo-endoscope in space;
- a user interface and a display;
- computing and storing means containing pre-operative radiologic data of a patient;

said system being characterized in that:
- the computing and storing means are configured to perform a registration between real-time intra-operative data and the pre-operative radiologic data and
- the display is configured to provide to the user a navigation view integrating real-time intra-operative data view within the pre-operative radiologic data based on said registration.

This disclosure presents a technical solution to overcome the above difficulties and provide intraoperative guidance for EUS procedure. It is the purpose of this disclosure to describe a method and a system to provide medical navigation.

We mean by echo-endoscope, an endoscope comprising an ultrasound transducer and adapted to acquire a real-time ultrasound signal. For example, the echo-endoscope is adapted to acquire an ultrasound image. The echo-endoscope can also be configured to acquire a real-time optical or video signal.

By real-time intra-operative data, we mean data acquired during the echo-endoscopic procedure. Real time intra-operative may comprise ultrasound and/or optical data acquired by the endoscope and/or tracking data acquired by the tracking device.

By user interface and a display, we mean an interface adapted to provide information to the user and adapted to gather information or commands from the user.

By pre-operative data, we mean data acquired before the ultrasound endoscopy.

We mean by radiologic data, images or other medical data acquired by a medical device. For example, the radiologic data can be provided by a 3D imaging tool such as a Computed Tomography (CT) image, a Magnetic Resonance Image (MRI) or a Positron Emission Tomography (PET) image.

By registration between real-time intra-operative data and pre-operative radiologic data, we mean identifying a given anatomical landmark or structure in both intra-operative and pre-operative data.

In other words, the registration between real-time intra-operative data and pre-operative data is a transformation of spatial coordinates, transforming the endoscope or tracking system spatial coordinates into the patient spatial coordinates.

By navigation view, we mean a representation of intra-operative data and/or pre-operative radiologic data. Intra-operative and pre-operative data can be simultaneously displayed thanks to the registration performed by the system according to the invention.

Advantageously, the medical navigation system according to the invention perform such a registration in an efficient and reliable way with minimal clinical workflow interruption.

Advantageously, the medical navigation system according to the invention displays an efficient navigation view which is simply to use also for an unskilled operator. The medical navigation view according to the invention allows an unskilled operator to navigate the echo-endoscope towards a predefined anatomical region.

For example, the system according to the invention is configured to compute the real-time position and orientation of the ultrasound signal with respect to the radiologic data. In other word, the system is adapted to transform the endoscope or tracking system spatial coordinates system into the patient spatial coordinates system, allowing for the real-time registration of the ultrasound signal and the radiological data.

Advantageously, the system for medical navigation according to the invention is easy to use and does not require a highly skilled operator.

According to an embodiment, the computing and storing means of the medical navigation system according to the invention are configured to perform a first registration computation and a registration refinement.

The system for medical navigation according to the invention may also have one or more of the characteristics below, considered individually or according to all the technically possible combinations thereof:
  the ultrasound signal is an ultrasound image;
  intra-operative data comprise: ultrasound signals acquired by the echo-endoscope and/or video signal acquired by the echo-endoscope and/or tracking signal acquired by the tracking device;
  computing means are configured to compute a real-time position and orientation of the ultrasound signal with respect to the pre-operative radiologic data;
  the display is configured to provide to the user a navigation view integrating the ultrasound real-time view within the pre-operative radiologic data based on said position and orientation;
  the tracking system or device is further configured to define a tracking reference frame and provide the position and orientation of the distal tip of the endoscope within said tracking reference frame;
  the tracking system comprises an electromagnetic tracking device or a fibre-optic tracking device;
  it comprises means for selecting a landmark in the ultrasound signal and for identifying and marking said landmark on the pre-operative data;
  the computing and storing means are configured to perform a registration between the ultrasound signal and the pre-operative data, said registration being based on the selected landmark;
  the registration is further based on one additional anatomical information;
  the additional anatomical information comprises an anatomical axis or landmark;
  the additional anatomical information comprises the esophagus position and orientation;
  the system further comprises a tracked pointer tracked by the tracking device;
  the system is configured to perform a first registration computation and a registration refinement;
  the system is configured to perform a first registration computation comprising an anatomical landmark localization, a patient axis identification and a registration based on at least an anatomical landmark and at least a patient axis, the anatomical landmark being internal or external;
  the system is configured to perform a registration refinement comprising an ultrasound anatomical landmark localization, an optical landmark localization and a locally-rigid alignment between the ultrasound anatomical landmark and the optical landmark;
  the computing and storing means are configured to perform a first registration computation and a registration refinement;
  the computing and storing means are configured to perform a first registration computation comprising an external anatomical landmark localization, a patient axis identification and a registration based on at least an external anatomical landmark and at least a patient axis;
  the computing and storing means are configured to perform a registration refinement comprising an ultrasound anatomical landmark localization, an optical landmark localization and a locally-rigid alignment between the ultrasound anatomical landmark and the optical landmark.

Another object of the invention is a method for medical navigation comprising the following steps:
  acquiring, by means of an echoendoscope, a real-time ultrasound signal and/or a video signal;
  tracking the distal tip of the echoendoscope;
  receiving and storing a preoperative radiologic data of a patient;
  performing a registration between intra-operative data and the pre-operative radiologic data and
  based on said registration, displaying a navigation view integrating real-time intra-operative data view within the pre-operative radiologic data.

The method for medical navigation according to the invention may also comprise one or more of the steps below, considered individually or according to all the technically possible combinations thereof:
  acquiring, by means of an ultrasound transducer or echo-endoscope, an ultrasound signal or image;
  tracking the distal tip of the ultrasound transducer;
  computing the position and orientation of the ultrasound signal or image with respect to the pre-operative radiologic data;

displaying a navigation view integrating the ultrasound signal within the pre-operative radiologic data based on said position and orientation.

it comprises a step of registering the ultrasound signal and the preoperative radiologic data;

the registration step comprises a first registration computation and a registration refinement;

the first registration computation comprises an anatomical landmark localization step, a patient axis identification step and a registration step based on at least an anatomical landmark and at least a patient axis, the anatomical landmark being external or internal;

the registration refinement comprises an ultrasound anatomical landmark localization step, an optical landmark localization step and a locally-rigid alignment step between the ultrasound anatomical landmark and the optical landmark;

performing the echo-endoscopic procedure using the displayed navigation view.

LIST OF FIGURES

Other characteristics and advantages of the invention will become clear from the description given below for indicative purposes and in no way limiting, with reference to the appended figures, among which:

DETAILED DESCRIPTION OF THE INVENTION

Figure 1:
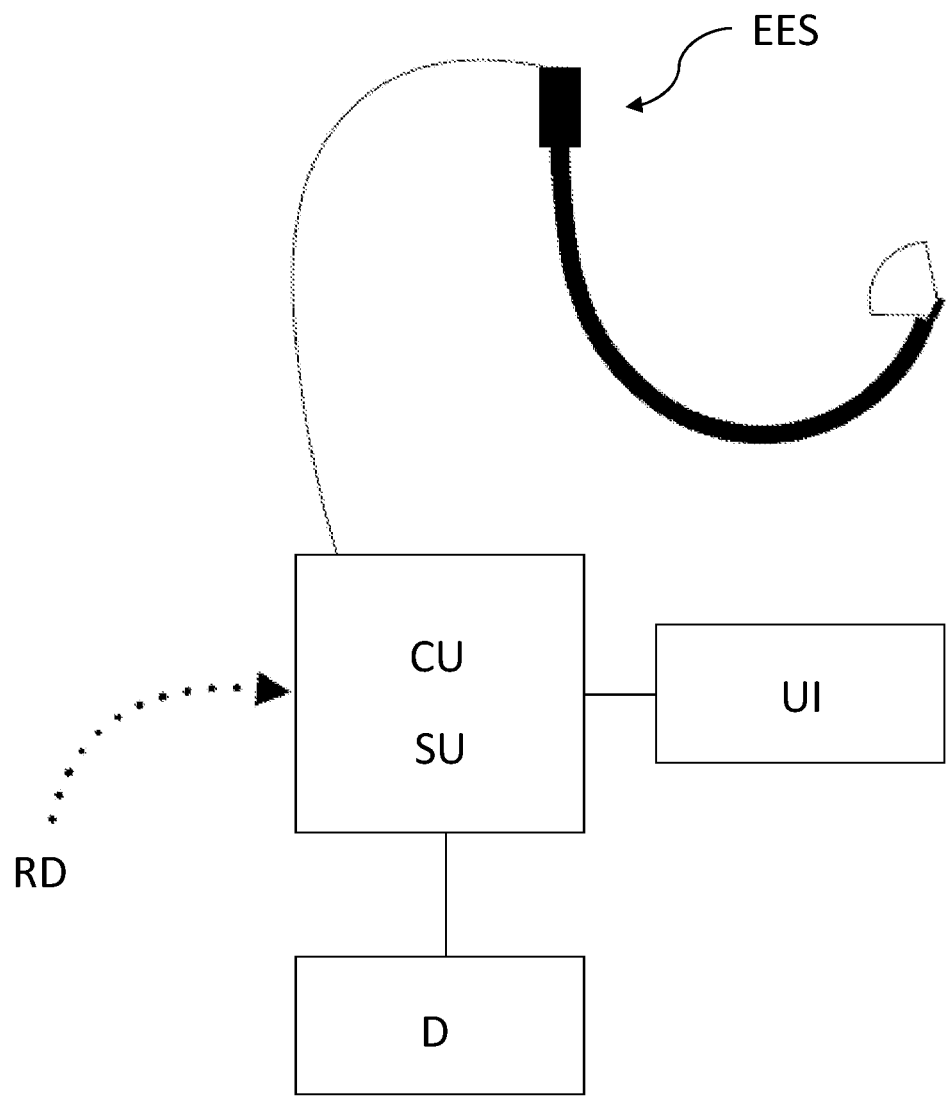
FIG. 1 shows a sketch of the medical navigation system according to the invention.

With reference to FIG. 1, the system for medical navigation described herein comprises an echoendoscope EES, a tracking system or device adapted to track the distal tip of the echo-endoscope in space, a user interface UI, a display D and computing unit CU and storing unit SU containing at least an algorithm and a preoperative radiologic data RD of a patient. The computing and storing units can also be merged in an computing and storing unit. The echoendoscope EES is adapted to acquire an ultrasound signal such as an ultrasound image. The system is adapted to compute the live position and orientation of the real-time ultrasound images with respect to the pre-operative radiologic data and display to the user a navigation view integrating the ultrasound live view within the pre-operative radiologic data based on said position and orientation.

Figure 2:
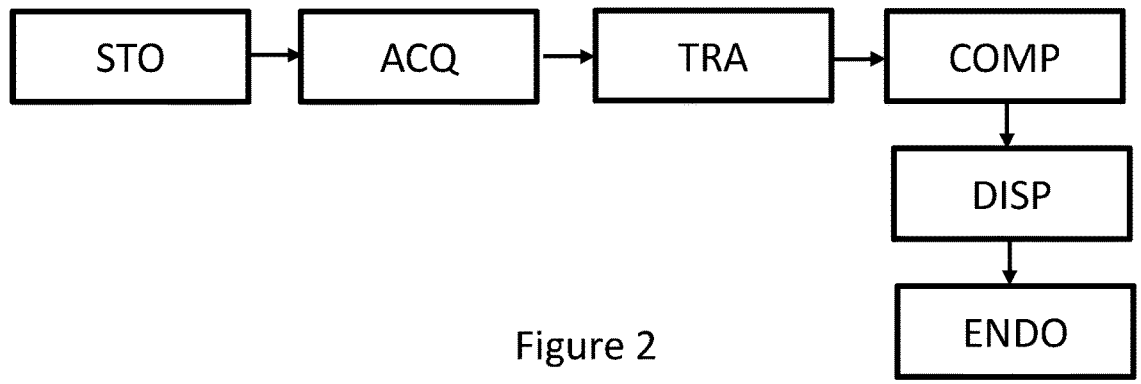
FIG. 2 shows a sketch of the medical navigation method according to the invention.

With reference to FIG. 2, the medical navigation method described herein comprises the steps of:

Providing a system for medical navigation comprising an echo-endoscope, a tracking system or device adapted to track the distal tip of the echo-endoscope in space, a user interface, a display and computing and storing means containing at least an algorithm;

Importing STO pre-operative radiologic data of a patient;

Start an echo-endoscopic procedure ACQ on the patient;

Tracking TRA the distal tip of the endoscope;

Computing COMP the live position and orientation of the live ultrasound images with respect to the preoperative radiologic data;

Display DISP to the user a navigation view integrating the ultrasound live view within the pre-operative radiologic data based on said position and orientation;

Perform ENDO the echo-endoscopic procedure using the displayed navigation view.

The system disclosed herein comprises an echoendoscope EES and a tracking device or system defining a tracking reference frame and providing the 3D position and orientation of the distal tip of the endoscope within this reference frame.

The tracking device or system is in communication with the computing CU and storing SU units in such a way that 3D position and orientations data can be sent to, interpreted and stored by the computing CU and storing SU unit. As the endoscope's tip shape and dimensions are known, the computing and storing means are configured to associate any point contained in any live ultrasound image to the live position of this point within the tracking reference frame.

In the rest of this document will refer to using the user interface to select a point within a live US image and having the computing and storing unit record the selected point position within the tracking reference frame as "selecting a point within the US image".

In different embodiments, the tracking method for the EES probe is based on electromagnetic properties (EM tracking) or another type of tracking (i.e. fiber-optic tracking). According to an embodiment, the tracking device comprises an EM tracking device or a fibre-optic tracking device.

It is an object of the present invention to provide a system providing guidance during EUS procedure by helping the user navigating the patient's anatomy based on 3D radiologic data acquired before the EUS procedure. During EUS procedures, navigating to a pre-determined precise location within the body of a patient requires expert skills. It is thus not useful to implement a navigation system for EUS requiring, as part of the registration process, the user to navigate to a pre-determined precise location within the body.

We will now describe several embodiments concerning the registration process.

In one general embodiment, the system for medical navigation described herein comprises means for the user to select landmarks during the EUS procedure using the user interface and then identify and mark the equivalent landmark on pre-operative radiologic data.

According to an embodiment, the registration is done in two steps and within each step an anatomical landmark matching is performed. The anatomical landmark matching can be performed manually by the operator. Alternatively, the landmark matching is performed by the computing and storing means.

The algorithm stored in the computing and storing unit completes a registration.

In other words, the system according to the invention is further configured to register the pre-operative radiological data and the real-time ultrasound images acquired by the echo-endoscope EES.

According to this embodiment, the system for medical navigation according to the invention comprises a tracked ultrasound endoscope EES, a display D, a user interface UI and a computing unit CU, the computing unit containing at least an algorithm and a pre-operative radiologic data of a patient, wherein the system is configured for a user to select landmarks within US images during a procedure on a patient using the user interface, select the matching anatomical landmark position within the pre-operative radiologic data of the patient using the user interface, the computing and storing unit computes a registration between the two positions by means of the at least one algorithm, computing a 3D visualization of the pre-operative radiologic data of the patient, computing the live position and orientation of the US image with respect to the preoperative radiologic data of the patient and displaying to the user a live view integrating within the 3D visualization of the pre-operative radiologic data, the live US image of the patient at the computed position and orientation within the 3D visualization of the pre-operative scan.

The medical navigation method according to the invention comprises the steps of:

Providing a guidance system including a computing unit and a tracked EUS probe;
Storing patient pre-operative radiologic data of the broad region of interest;
Navigating the US endoscope to the broad region of interest and select targeted anatomical points easy to identify on both the US image and the pre-operative radiologic data;
Selecting the matching landmarks in the pre-operative radiologic data;
Computing a rigid registration between the tracked scope reference frame and the preoperative dataset reference frame;
Computing a 3D visualization of the pre-operative radiologic data;
Embedding the live US images within the 3D visualization based on the registration information;
Displaying the 3D visualization of the pre-operative radiologic data with the embedded US image.

In another general embodiment, the registration process integrates additional anatomical information other than the landmark selected by the user. Such an embodiment is interesting as it may speed-up or increase the precision of the registration. For example, the system can use automatic recognition of anatomical structure. An example of additional anatomical structure is the esophagus.

The recognition of an anatomical structure or landmark can be done on intra-operative data. Intra-operative data comprises US data, endoscopic data such as optical or video data and data from the tracking device.

We consider the case of upper digestive echoendoscopy to illustrate this embodiment. The concept here is to automatically recognize anatomical structure as a preliminary step of the registration. The automatic recognition can be based on automatic recognition of anatomical shapes based on the tracking device data. The automatic recognition can be based on the recognition of anatomical landmark using the video images. In a dependent embodiment, the computing and storing unit contains an extraction algorithm adapted to automatically identify and extract the esophagus position and direction within the pre-operative radiologic data and a recognition algorithm adapted to identify the live esophagus position and orientation by identifying, during the EUS procedure, the moment when the esophagus is explored by the endoscopist. The esophagus exploration is isolated from the rest of the procedure based on the anatomical and operational characteristics for example: the exploration happens at the beginning of the procedure; the displacement is substantially rectilinear along a 20 cm path.

The computing and storing unit, using the registration algorithm, then performs a partial registration by matching the direction of the esophagus automatically extracted from the pre-operative radiologic scan together with live esophagus position and orientation identified during the procedure.

The registration can then be completed following any other embodiment described herein. It will be understood by the man skilled in the art that such an embodiment may be applied to other anatomical structures by adapting the isolation criterion of shape, size and/or procedure timing.

In another embodiment, the computing and storing unit contains an extraction algorithm adapted to automatically extract a landmark position and orientation within the pre-operative radiologic data and a video recognition algorithm adapted to identify a landmark position and orientation by identifying, during the EUS procedure, the video frames containing the landmark and recording the coordinate of the tracking device. The computing and storing unit, using the registration algorithm, then performs a partial registration or first registration computation by matching the direction and position of the landmark extracted from the preoperative radiologic scan together with landmark position and orientation identified during the procedure. The registration can then be completed by a registration refinement step following any other embodiment described herein.

In another general embodiment, the system integrates means to complete part of the registration using external patient landmarks. Such an embodiment leads to a quicker registration. In such an embodiment, the system further comprises a tracked pointer tracked by the tracking device. The user can select the position of a landmark external to the patient body from the pre-operative radiologic data using the user interface and then point the corresponding landmark position using the tracked pointer. The computing and storing unit, using the registration algorithm, then performs a partial registration by matching the landmark position selected from the pre-operative radiologic data together with the landmark position marked with the tracked pointer. The registration can then be completed following any other embodiment described herein.

The system and method for medical navigation described herein are meant to be used by endoscopists not experts in EUS. These users are typically gastroenterologists or surgeons and are typically not proficient at interpreting and understanding raw CT or MRI image slices and/or not highly skilled in the visual interpretation of EUS US and/or endoscopic images. Few image file standards have been adopted widely, only raw CT or MRI images can be exchanged across systems.

In one general embodiment, the computing and storing unit comprises a visualization algorithm adapted to compute a 3D visualization of the pre-operative radiologic raw data, the 3D visualization being then displayed to the user for him to select at least one landmark during the EUS procedure to complete the registration. Once the registration completed, the live US image is displayed to the user embedded within the 3D visualization of the pre-operative radiologic raw data. The live US image embedded within the 3D visualization of the pre-operative radiologic raw data will from now on be called the navigation visualization.

In one dependent embodiment, the navigation visualization will be oriented in real time to match the point of view as seen from the tip of the scope.

In one dependent embodiment, the 3D visualization will be computed at the beginning of the procedure and a sub-set of the 3D visualization only will be displayed to the user.

In one dependent embodiment, the navigation visualization contains the 3D visualization of the preoperative radiologic image, which is cut along the plane of the live US image, to show the section of the 3D visualization being currently imaged.

In one general embodiment, the navigation visualization further integrates the live endoscopic view recorded by the camera placed at the distal tip of echo-endoscopes. During an EUS procedure with the presently described system, the position and orientation of the endoscope tip is known. After the registration process, the position and orientation of the endoscopic image with respect to the preoperative radiologic image is known. The live endoscopic view can thus be embedded with a realistic position and orientation within the 3D visualization of the pre-operative radiologic image.

In a general embodiment, the pre-operative radiologic data can be a pre-operative image set (CT or MR), or a 3D skin surface model automatically segmented from a pre-operative image (CT or MR), or a segmented pre-operative 3D image (CT or MR), or a 3D skin surface model automatically made before examination, or a biomechanical pre-operative model (CT or MR) accounting for soft-body changes.

In one embodiment, the method additionally comprises a step of pre-operative planning. The preoperative radiologic data, reconstructed or not can be annotated or enhanced by the user before it is used as input in the system. This step could allow for example the user to carefully examine the pre-operative data and identify relevant structures such as lesion to be biopsied or ablated and anatomical landmarks used for registration purposes.

In one embodiment, the user interface allows the user turn on and off, the display of the pre-operative radiologic data. The user input interface may also be used to amend the visualization of the pre-operative radiologic data, for example switching between different visualization modes such as color maps, label maps, adjusting transparency, modify the part of the segment model that is displayed and changing the visualization viewpoint characteristics (angle, zoom etc.). The man skilled in the art will identify display modes.

The man skilled in the art will appreciate that any type of EUS know in the art might be used for the system and method for medical navigation described herein. For example, EUS probe can vary between linear EUS, two-dimensional EUS or tridimensional EUS as well as radial, frontal or lateral viewing EUS.

According to an embodiment, the system for medical navigation can be described as the following system:

A system for medical navigation providing guidance during an endosonographic procedure on an anatomical zone in a patient subsequent to a 3D radiological scan of the same anatomical zone in the same patient has been acquired thus generating a pre-operative radiologic raw data, said medical system comprising:
i) An endoscopic ultrasound system with an ultrasonic endoscope which during an endosonographic procedure generates video images and ultrasound images
ii) A display and user interface
iii) A tracking device or system defining a tracking reference frame, providing the 3D position and orientation of the end tip of the ultrasonic endoscope within this tracking reference frame
iv) Computing and storing means
wherein said computing and storing means are configured to retrieve the "pre-operative" radiologic raw data, wherein computing and storing means are configured to associate any point contained in any of said ultrasound images to a coordinate within said tracking reference frame, characterized in that the medical system is configured to
i) Compute a 3D visualization of the pre-operative radiologic raw data,
ii) Provide an interface for the user, during an endosonographic procedure, to select and tag at least one landmark position within ultrasound images, the system storing the 3D position of the US landmark together with the associated marked ultrasound image,
iii) Provide an interface for the user to select the anatomical position of the at least one landmark, within the "pre-operative" radiologic raw data or the 3D visualization,
iv) Compute a spatial correspondence between the "pre-operative" radiologic raw data and the tracking reference frame based on the landmark positions within the pre-operative radiologic raw data and the tracking reference frame Computing and displaying in real time to the user a live navigation view integrating the live US image within said 3D visualization of the pre-operative radiologic raw data, the live US image being positioned and oriented to match its actual live position and orientation.

Figure 3:
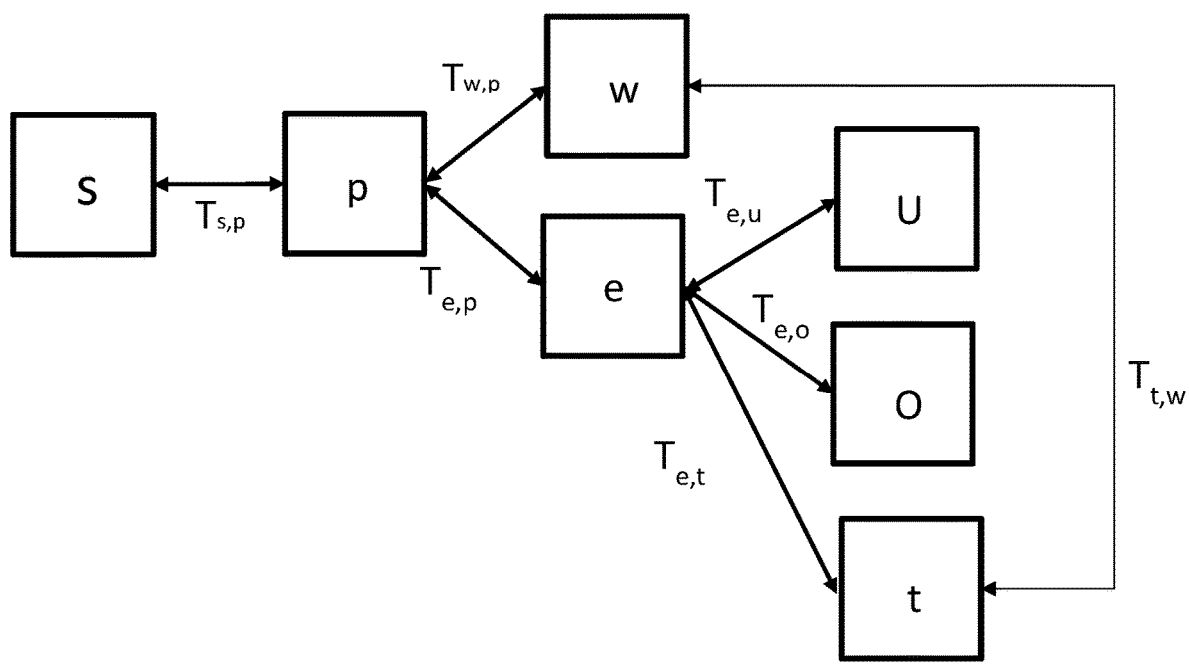
FIG. 3 shows a sketch of the different spatial coordinate systems involved in the realization of the method according to the invention.

FIG. 3 shows the different coordinate systems involved in the application of the system and method according to the invention.

Based on FIG. 3, is it possible to describe the implementation of the registration system and method. The objective of this system is to solve a challenging computational problem: fast and reliable registration with minimal clinical workflow interruption.

FIG. 3 sketches the coordinate transforms between source data s, patient p, endoscope e, ultrasound image u optical image o, tracking sensor t, and the world coordinates w. World coordinates are defined as the tracking system's coordinate system. In this document, source data, pre-operative data and pre-operative radiologic data refer to the same data.

We use the following coordinate system definitions:

Source data coordinates: 3D source data are the medical image data that will be registered and visualized for computer-assisted procedure navigation. The 3D source data is generated by a 3D imaging system, including but not limited to the following:
Computed Tomography (CT) image
Magnetic Resonance (MR) image
Positron Emission Tomography (PET) image The 3D source data can be acquired either pre-operatively during a diagnostic examination, or intra-operatively during the EUS procedure. The source data may be pre-processed for enhanced visualization using one or more processed, including, but not limited to:
3D segmentation, computed with either human experts or automatically with an AI-based segmentation system
Image transformations, such as cropping, scaling or intensity windowing
Source data fusion, combining different source images in patient coordinates, World coordinates: We define world coordinates as the coordinate system of the endoscope's tracking device. The tracking device is required to, at a minimum, produce real-time 6 Degree-of-Freedom (DoF) 3D poses (rotation and orientation) of the probe's tip in world coordinates. Compatible tracking devices include, but are not limited to the following:

Endoscopes with an embedded 6DoF EM tracking device at the tip

Endoscopes with an embedded chain of EM sensors within the scope, including a 6DoF EM tracking device at the tip Endoscopes with a 6DoF EM tracking device fixed in the auxiliary channel distal end.

Endoscopes with a 6DoF EM tracking device fixated externally on the endoscope tip using a cap Endoscopes with an embedded 6DoF fibre optic tracking system Robotically controlled endoscope with known scope tip position provided by kinematics.

Ultrasound coordinates: This is the coordinate frame of the endoscope's ultrasound image.

Optical coordinates: This is the coordinate frame of the endoscope's optical image.

Tracking sensor coordinates: This is the coordinate frame of the tracking sensor at the tip of the endoscope.

Patient coordinates: This is the canonical coordinate frame that were all data is registered to. Patient coordinates has three primary axes: anterior/posterior, left/right, superior/inferior axis.

The following transformations are known and can be computed in processes external to the registration process:

Endoscope-to-tracking sensor transform $(T_{e,t})$. Without loss of generality, we define endoscope coordinates as the same as tracking sensor coordinates, meaning that $(T_{e,t})$ is the identity transform. This is possible because we assume the tracking sensor is rigidly fixed relative to the endoscope tip, and therefore it does not change over time.

Endoscope-to-ultrasound image transform $(T_{e,u})$. Because the endoscope tip is rigid, this does not change over time and is computed with a one-time external calibration process, for example hand-eye calibration [PlusToolkit].

Endoscope-to-optical image transform $(T_{e,o})$. Because the endoscope tip is rigid, this does not change over time and is computed with a one-time external calibration process, for example hand-eye calibration [X].

Tracking sensor-to-world transform $(T_{t,w})$. This is provided by the tracking sensor. Unlike the above transforms, this is time-variant and is provided by the 3D tracking system.

Source data-to-patient transform $(T_{s,p})$. We assume the patient is imaged in the source data in the supine position, meaning the patient axes is approximately aligned with the scanner's axes. This occurs in the overwhelming majority of cases. When there is only one source image, we define source data and patient coordinates as the same. When there are multiple source images (e.g. MR and CT), these require co-registration.

The unknown coordinate transform is the time-varying endoscope-to-patient $(T_{e,p})$ transform. This is determined by composing the endoscope-to-world transform (known) with the world-to-patient transform $(T_{w,p}$: unknown). The registration process according to the invention gives a novel, fast and reliable solution to compute $T_{w,p}$ with minimal clinical workflow interruption.

According to an embodiment, the registration step comprises two further steps:

Initial Registration Computation. This process computes a first world-to-patient transform using external or internal anatomical landmarks and patient axis information.

Registration Refinement. This process improves on the initial registration by updating it using information from internal anatomical or pathological landmarks as they are identified during the procedure.

We now describe these processes in detail. We first define various physical and virtual entities:

Patient Graphical User Interface PGUI: The software component for interactive fusion imaging and virtual reality display of all relevant information (source data, endoscope, ultrasound and optical images) in patient coordinates. The GUI is used during registration for interactive registration, as described below.

Picker Device: A hand-held device with a pointed tip that is used to localize external anatomical landmarks in world coordinates. This can be a dedicated picker device provided by the 3D tracker system, or it can be the endoscope tip. The advantage of using the endoscope as the picker device is that it eliminates an additional device in the operating room, but at the price of lower-accuracy compared to a dedicated picker device.

External anatomical landmark EAL: An anatomical landmark that can be repeatably located in both the source data and on the external surface of the patient during the procedure. For abdominal procedures, good EALs are those that are relatively stable to breathing motion and other physiological movement. These include, but are not limited to, the sternum body and sternum base.

Ultrasound anatomical landmark UAL: An anatomical landmark that can be located in both the source data and in EUS ultrasound images the procedure. For abdominal procedures, our possible UALs include, but are not limited to, the cardia, gastro-esophigal junction, duodenal papilla, pancreas head, and tail, aorta, and aorta/celiac trunk junction.

Optical anatomical landmark OAL: An anatomical landmark that is can be located in both the source data and in the endoscope's optical images during the procedure. For abdominal procedures, our OALs include, but are not limited to, the cardia and the duodenal papilla.

Anatomic Landmark AL: Includes EAL, UAL and OAL.

Intra-operative EAL, UAL and OAL position: The 3D position of a EAL, UAL or OAL defined in their respective coordinate systems (world, ultrasound image and optical image respectively).

Intra-operative EAL, UAL and OAL covariance matrix: An evaluation of the confidence of an EAL, UAL or OAL position. This is implemented using a 3×3 covariance matrix, where larger values in the covariance matrix indicates greater uncertainty in the landmark position.

Source Anatomical Landmark (SAL) position: The 3D position of a EAL, UAL or OAL located in the source data, and defined source data coordinates.

SAL covariance matrix: An evaluation of the confidence of a SAL position. This is implemented using a 3×3 covariance matrix.

Convolutional Neural Network (CNN): A popular type of artificial neural network that has neurons arranged in convolutional patterns.

Figure 4:
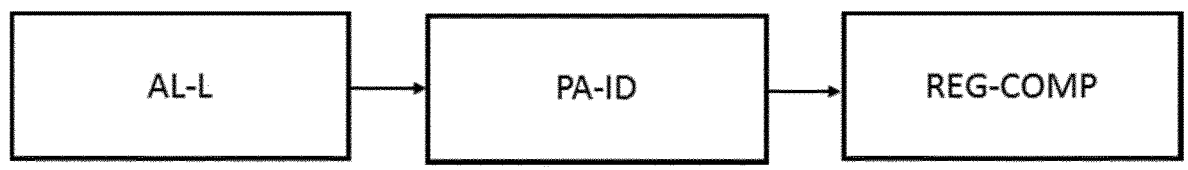
FIG. 4 shows a sketch of the initial registration computation step comprised in the method according to the invention.

The initial registration step or computation is illustrated in FIG. 4. The initial registration comprises three steps as described below.

Anatomic Landmark localization—AL-L. The purpose of this step is to determine a set of matching Anatomic Landmarks ALs in source data and world coordinates. For external landmarks in world coordinates, the picking or picker device is used. For internal or external landmarks in source data coordinates, landmarks are located using one of the following mechanisms:

Manual localization. These are determined using a human operator using the PGUI.

Automatically located ALs. These are determined using an AI system, typically a CNN, that can automatically localize anatomical landmarks in the source data. The main advantage compared to manual localization is reduced workflow interruption.

Automatically located EALs are visualized to a human operator in the PGUI and the human operator verifies their correctness. If deemed incorrect, the human operator can relocate them with manual localization.

Patient Axis Identification—PA-ID. If there are three or more matched EALs, it is possible to estimate the world-to-patient transform using rigid body alignment of the landmarks using the Singular Value Decomposition (SVD). However, this is undesirable because of the time required to localize, and the difficulty in finding three stable landmarks. To resolve this difficulty, we allow for fewer EALs (at least one is required), and we complement this with additional patient axis information. With fewer EALs, we require more axis information in order to resolve the word-to-patient transform.

The relationship between the number of EALs and the number of required patient axes that must be determined in order to uniquely compute the world-to-patient coordinate transform is the following. If three EALs are matched, zero patient axes are required. If two EALs are matched, one patent axis is required. If one EAL is patched, two patent axis are required.

We now describe our approach for determining the patient axes given 1 EAL. We consider two cases based on the Supine position.

We exploit the fact that normal vector of the patient table corresponds with the posterior/anterior axis. Consequently, to determine this axis, we require to determine the normal vector of the patient table. In general, we compute this by having a human operator to use the picking device to touch any three non-colinear points on the patient table. From these points the plane's normal is computed using the SVD. In the special case of using an EM tracking device, we have an even simpler solution, provided that the tracking device field generator is positioned either on the patient table, or on a surface parallel to the patient table. When this is done, the posterior/anterior axis is given immediately by one of the axes of the tracking device system.

We then compute the superior/inferior axis. We describe two solutions to this with very simple operator workflows. The operator is free to choose which solution they prefer to use.

Solution 1: Axis Tracing

The human operator traces a line down the sternum using the picking device. This generates a sequence of 3D points along the sternum, which we virtually project onto the patient table plane, to form a path of 2D points on the virtual table plane. Finally, a robust line-fitting algorithm is used to estimate the best-fitting line passing through the 2D points (Random sample consensus, RANSAC), and the direction of this line gives the superior/inferior axis.

Solution 2: Endoscope Tip Alignment

The human operator places the endoscope tip on the patient's sternum with the US probe aligned with the superior/inferior axis. One done the endoscope's 3D position is recorded using the tracking device, and the 3D position of the US image plane is determined in world coordinates. Finally, the superior/inferior axis is determined by intersecting the US image plane with the table plane.

Transform Computation-REG-COMP

The left/right patient axis is then computed by the cross-product of posterior/anterior and superior/inferior axes. Given the EAL and the three patient axes, we have sufficient information (6 geometric equations) to compute world-to-patient coordinate transform (6DoFs). We compute it using Horn's absolute orientation algorithm.

In the majority of cases the source data is acquired with the patient in the supine position, and as such the patient axes are aligned with the image coordinate system. In special cases where the patient is not scanned in the supine position, the axes are determined by one of two mechanisms. The first is by a human operator using the NGI, by interactively drawing 3D vectors in the source data corresponding to two of the three primary axes. From this data the third axis can be automatically determined using the vector cross-product. The second mechanism is to compute the axes using a trained AI system based on e.g. a CNN. Similarly to EAL-L or component 1, a visualization of this is provided to the human operator who verifies the results.

In non-supine positions, we determine the patient axis using tracking data from the EUS probe as it enters the GI tract. Specifically, we record the 3D position of the EUS probe tip over time as it passes down the esophagus to the stomach. This generates a 3D chain of points in world coordinates. In the source data, the esophagus centre axis is determined, either using manually with the PGUI, or automatically with an AI recognition system. This provides a 3D chain of points in patient coordinates. Finally, we perform a registration using the point chains and at least one external landmark (e.g. the sternum base), using robust Linear Least Squares point and path alignment.

The initial registration provides a coarse alignment, typically with fewer than two centimeters in accuracy for organs such as the pancreas that do not move considerably from breathing motion. This may be sufficient in Global Positioning System (GPS)-like applications, where the intention is to only give a rough visualization of the position and orientation of the EUS endoscope in patient coordinates. When a more accurate registration is desired, the registration refinement system is executed.

Figure 5:
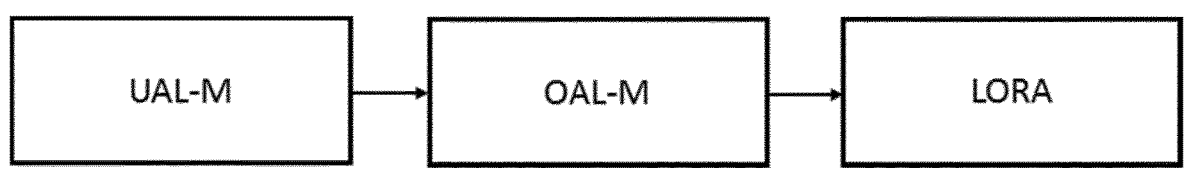
FIG. 5 shows a sketch of the registration refinement step comprised in the method according to the invention.

FIG. 5 shows the registration refinement step or procedure.

Registration refinement comprises three steps: Ultrasound Anatomic Landmark Matching UAL-M, Optical Anatomic Landmark Matching OAL-M and Locally-Rigid Alignement LORA.

Ultrasound Anatomic Landmark Matching UAL-M: during the procedure, when a UAL is encountered (see above definition for examples), it can be localized and used to improve registration. Localization can either be done with manual localization (where a human uses the PGUI to mark the landmark location in a US image). Alternatively, it can be done with automatic localization provided by an AI system that automatically recognizes UALs in US video. In addition to the landmark position, the confidence matrix is provided, which determines the amount of confidence in the landmark position. For manual localization, this is done with the PGUI by marking a zone around the landmark to denote the confidence. For automatic localization, the confidence matrix is outputted by the machine simultaneously with the landmark position.

When a UAL is localized, it is then localized in the source data (a Source Anatomical Landmark). Similarly to a UAL, a SAL is either determined manually using the PGUI or automatically with an AI landmark recognition system.

Optical Anatomic Landmark Matching OAL-M: Similarly to UAL-M, landmarks can also be located using the endoscope's optical image. The process is similar to UAL-M.

Locally-Rigid Alignment LORA: The purpose of this step is to automatically compute a time-varying registration matrix using all the landmarks that have been matched in steps UAL-M and OAL-M. It also uses the fixed set of matched landmarks used in the initial registration. The registration matrix is computed by solving a numerical optimization process. The registration is computed as a rigid 3D matrix with two characteristics:

1. The influence of landmarks of higher confidence have a greater influence on the registration matrix compared to landmarks of lower confidence
2. The influence of landmarks that are closer to the current position of the endoscope position have greater influence on the registration matrix. This allows physiological movement of distant landmarks to have less influence on the registration matrix.

Then an optimization process is performed. Specifically, we create a numerical search problem where the goal is to find the registration matrix that has both above properties, implemented as a numerical loss function. To satisfy 1, we search for registration matrix that minimizes the Jenson-Shannon divergence of each matched landmark, using the confidence matrices of the landmarks. To satisfy 2, we weight the loss function using exponential weighting, based on the distance of each landmark to the current 3D position of the endoscope in world coordinates.

The invention claimed is:

1. A system for medical navigation comprising an echo-endoscope, a tracking device, a pointer tracked by the tracking device, a user interface, a display and a computing and storing system, the computing and storing system containing pre-operative radiologic data of a patient, wherein the computing and storing system is configured to:
   receive, via the user interface, a first chain of points representing an oesophagus centre axis in the pre-operative radiologic data;
   receive, from the echo-endoscope, a second chain of points representing a position path of the tip of the echo-endoscope when the echo-endoscope passes between the oesophagus and the stomach of the patient;
   receive a localization, in the pre-operative radiologic data, of an anatomical landmark located on an external surface of the patient;
   receive a localization of the anatomical landmark acquired by the pointer and tracked by the pointer tracker;
   perform a registration between a first coordinate system related to the pre-operative radiologic data and a second coordinate system related to real-time intra-operative data acquired by the echo-endoscope, the registration being performed based on the first chain of points, the second chain of points and the received localizations of the anatomical landmark;
wherein
   the echo-endoscope is further configured to acquire, after the registration, a real-time ultrasound signal on the patient;
   the tracking device is further configured to acquire tracking data representative of a position of a distal tip of the echo-endoscope in a space during the acquisition of the real-time ultrasound signal;
   the computing and storing system is further configured to compute, based on the registration and the tracking data, a real-time position and orientation of the real-time ultrasound signal with respect to the pre-operative radiologic data based on said registration; and
   the display is configured to display a navigation view integrating a real-time ultrasound data view within the pre-operative radiologic data based on said position and orientation.

2. The system for medical navigation according to claim 1, wherein the system is further configured to perform a registration refinement comprising: receiving at least one localization of at least one respective ultrasound anatomical landmark, receiving at least one localization of at least one respective optical landmark and performing a locally-rigid alignment using the at least one ultrasound anatomical landmark and the at least one optical landmark.

3. The system for medical navigation according to claim 1, wherein the tracking device is an electromagnetic tracking device or a fibre-optic tracking device.

4. The system for medical navigation according to claim 1, wherein the anatomical landmark located on the external surface of the patient is a sternum body or the sternum base of the patient.

5. The system for medical navigation according to claim 1, wherein the localization, in the pre-operative radiologic data, of an anatomical landmark is received through the user interface or is determined automatically using artificial intelligence.

6. A method for medical navigation comprising:
   receiving a pre-operative radiologic data of a patient;
   receiving a first chain of points representing an esophagus centre axis in the pre-operative radiologic data;
   acquiring, by an echo-endoscope, a second chain of points representing a position-path of a tip of the echo-endoscope when the echo-endoscope passes between the esophagus and the stomach of the patient;
   receiving a localization, in the pre-operative radiologic data, of an anatomical landmark located on an external surface of the patient;
   receiving a localization of the anatomical landmark acquired by a pointer and tracked by a pointer tracker;
   performing a registration between a first coordinate system related to the pre-operative radiologic data and a second coordinate system related to real-time intra-operative data acquired by the echo-endoscope, the registration being performed based on the first chain of points, the second chain of points and the received localizations of the anatomical landmark;
   after the registration, acquiring, by the echo-endoscope, a real-time ultrasound signal on the patient;
   acquiring tracking data representative of a position of a distal tip of the echo-endoscope during the acquisition of the real-time ultrasound signal;
   computing, based on the registration and the tracking data, a real-time position and orientation of the real-time ultrasound signal with respect to the pre-operative radiologic data; and
   displaying a navigation view integrating a real-time ultrasound data view within the pre-operative radiologic data based on said position and orientation.

7. The method for medical navigation according to claim 6, further comprising a registration refinement, said registration refinement comprising: receiving at least one localization of at least one respective ultrasound anatomical landmark, receiving at least one localization of at least one respective optical landmark, and performing a locally-rigid alignment step using the at least one ultrasound anatomical landmark and the at least one optical landmark.

8. The method for medical navigation according to claim 6, wherein the anatomical landmark located on the external surface of the patient is a sternum body or the sternum base of the patient.

9. The method for medical navigation according to claim 6, wherein the localization, in the pre-operative radiologic data, of an anatomical landmark is received through the user interface or is determined automatically using artificial intelligence.

* * * * *